US007519211B2

(12) United States Patent
El Fakhri et al.

(10) Patent No.: US 7,519,211 B2
(45) Date of Patent: Apr. 14, 2009

(54) FACTOR ANALYSIS IN MEDICAL IMAGING

(75) Inventors: Georges El Fakhri, Brookline, MA (US); Arkadiusz Sitek, Walnut Creek, CA (US)

(73) Assignees: The Brigham and Women's Hospital, Inc., Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 9 days.

(21) Appl. No.: 11/533,145

(22) Filed: Sep. 19, 2006

(65) Prior Publication Data

US 2007/0014463 A1 Jan. 18, 2007

Related U.S. Application Data

(62) Division of application No. 11/148,700, filed on Jun. 9, 2005, now Pat. No. 7,127,095.

(60) Provisional application No. 60/682,173, filed on May 17, 2005, provisional application No. 60/619,296, filed on Oct. 15, 2004.

(51) Int. Cl.
*G06K 9/00* (2006.01)
*G06K 9/38* (2006.01)
*G06K 9/62* (2006.01)

(52) U.S. Cl. ..................... 382/128; 382/272

(58) Field of Classification Search ............... 382/103, 382/154, 128–134, 164, 173, 190, 272, 276, 382/285, 262, 172; 250/394; 378/4, 8–9, 378/901; 128/623.1; 434/262, 272, 323; 600/431, 437, 483, 509
See application file for complete search history.

(56) References Cited

U.S. PATENT DOCUMENTS

| 4,974,598 | A | | 12/1990 | John | |
|---|---|---|---|---|---|
| 5,591,337 | A | * | 1/1997 | Lynn et al. | 210/489 |
| 5,633,951 | A | * | 5/1997 | Moshfeghi | 382/154 |
| 6,331,116 | B1 | * | 12/2001 | Kaufman et al. | 434/262 |
| 6,385,332 | B1 | * | 5/2002 | Zahalka et al. | 382/128 |
| 6,501,848 | B1 | | 12/2002 | Carroll et al. | |
| 6,690,816 | B2 | * | 2/2004 | Aylward et al. | 382/128 |
| 7,127,095 | B2 | * | 10/2006 | El Fakhri et al. | 382/128 |
| 7,194,117 | B2 | * | 3/2007 | Kaufman et al. | 382/128 |
| 2001/0031920 | A1 | * | 10/2001 | Kaufman et al. | 600/431 |
| 2001/0044099 | A1 | | 11/2001 | Rappaport | |
| 2003/0048937 | A1 | | 3/2003 | Gullberg et al. | |
| 2003/0095692 | A1 | | 5/2003 | Mundy et al. | |
| 2003/0223627 | A1 | * | 12/2003 | Yoshida et al. | 382/128 |

(Continued)

OTHER PUBLICATIONS

Buvat et al., "Target Apex-Seeking in Factor Analysis of Medical Image Sequences," Phys. Med. Biol., 38:123-138 (1993).

(Continued)

*Primary Examiner*—Amir Alavi
(74) *Attorney, Agent, or Firm*—Fish & Richardson P.C.

(57) ABSTRACT

A method for processing image data includes estimating initial factor images from image data, transforming the estimated initial factor images by a transformation variable to obtain transformed factor images, providing an objective function that is a function of the transformed factor images, and minimizing the objective function to obtain unique factor images from the estimated initial factor images.

12 Claims, 11 Drawing Sheets

U.S. PATENT DOCUMENTS

| | | | |
|---|---|---|---|
| 2005/0105768 A1 | 5/2005 | Yang et al. | |
| 2005/0286768 A1 | 12/2005 | Battle | |
| 2006/0000983 A1 | 1/2006 | Charron et al. | |
| 2006/0013505 A1 | 1/2006 | Yau et al. | |
| 2006/0083415 A1 | 4/2006 | El Fakhri et al. | |
| 2007/0014463 A1* | 1/2007 | El Fakhri et al. | 382/128 |

OTHER PUBLICATIONS

Chen et al., "Measurement of Cardiac Output with First-Pass Determination During Ribidium-82 PET Myocardial Perfusion Imaging," Eur. J. Nucl. Med., 23:993-996 (1996).

Coxson et al., "Consequences of Using a Simplified Kinetic Model for Dynamic PET Data," J. Nucl. Med., 38:660-667 (1997).

Dahl et al., "Myocardial Ribidium-82 Tissue Kinetics Assessed by Dynamic Positron Emission Tomography as a Marker of Myocardial Cell Membrane Integrity and Viability," Circulation, 93:238-245 (1996).

DeKemp et al., "Detection of Serial Changes in Absolute Myocardial Perfusion with $^{82}$Rb PET," J. Nucl. Med., 41:1426-1435 (2000).

Di Paola et al., "Handling of Dynamic Sequences in Nuclear Medicine," IEEE Trans. Nucl. Sci., 29:1310-1321 (1982).

Herrero et al., "Implementation and evaluation of a two-compartment model for quantification of myocardial perfusion with ribidium-82 and positron emission tomography," Circ. Res., 70:496-507 (1992).

Houston, "The Effect of Apex-Finding Errors on Factor Images Obtained from Factor Analysis and Oblique Transformation," Phys. Med. Biol., 29:1109-1116 (1984).

Knesaurek et al., "Comparison of 2-Dimensional and 3-Dimensional $^{82}$Rb Myocardial Perfusion PET Imaging," J. of Nuc. Med., 44:1350-1356 (2003).

Lin et al., "Quantification of Myocardial Perfusion in Human Subjects Using $^{82}$Rb and Wavelet-Based Noise Reduction," J. Nucl. Med., 42:201-208 (2001).

Samal et al., "On the Existence of an Unambiguous Solution in Factor Analysis of Dynamic Studies," Phys. Med. Biol., 34:223-228 (1989).

Sitek et al., "Factor Analysis with a Priori Knowledge-Application in Dynamic Cardiac SPECT," Phys. Med. Biol., 45:2619-2638 (2000).

Sitek et al., "Correction for Ambiguous Solutions in Factor Analysis Using a Penalized Least Squares Objective," IEEE Trans. Med. Imag., 21:216-225 (2002).

Sitek et al., "Removal of Liver Activity Contamination in Teboroxime Dynamic Cardiac SPECT Imaging with the Use of Factor Analysis," J. Nucl. Cardiol., 9:197-205 (2002).

International Search Report, mailed Apr. 12, 2006 for PCT Application PCT/US05/36842 filed on Oct. 14, 2005.

* cited by examiner

| S | Gender | Age | Prior CAD | BP (mm Hg) | HR (bpm) | SSS | K1(ml/min/g) | CFR | k2(1/min) | Catheterization results |
|---|---|---|---|---|---|---|---|---|---|---|
| S1 | F | 89 | no | 122/73 - 106/59 | 78 - 94 | 0 | 0.80 - 1.84 | 2.3 | 0.015 - 0.028 | NA |
| S2 | F | 83 | no | 99/61 - 107/54 | 66 - 87 | 0 | 0.69 - 1.48 | 2.14 | 0.013 - 0.024 | NA |
| S3 | F | 76 | no | 145/80 - 131/65 | 74 - 83 | 0 | 0.64 - 1.34 | 2.09 | 0.012 - 0.039 | NA |
| S4 | F | 93 | no | 197/50 - 166/65 | 71 - 75 | 0 | 0.73 (rest) | NA | 0.020 (rest) | NA |
| S5 | F | 43 | no | 107/60 - 99/48 | 61 - 87 | 0 | 1.07 (rest) | NA | 0.013 (rest) | NA |
| S6 | M | 78 | no | 143/71 - 119/51 | 69 - 63 | 0 | 1.82 (stress) | NA | 0.022 | NA |
| S7 | M | 65 | no | NA | NA | 0 | 1.03 (rest) | NA | 0.014 | NA |
| S8 | M | 56 | yes | NA | NA | NA | 0.61 (rest) | NA | 0.015 | 80% LAD, 80% LCX, 90% RCA |
| S9 | M | 66 | yes | 127/65 - 109/62 | 65 - 72 | 27 | 0.53 - 0.87 | 1.6 | 0.013 - 0.018 | NA |
| S10 | M | 81 | yes | 138/68 - 100/56 | 71 - 91 | 26 | 0.52 - 0.74 | 1.43 | 0.011 - 0.014 | 100% LAD, 90%RCA |
| S11 | F | 76 | yes | 117/62 - 116/54 | 58 - 62 | 28 | 0.61 - 0.84 | 1.39 | 0.012 - 0.016 | grafts patent |
| S12 | M | 60 | no | 203/98 - 127/98 | 77 - 97 | 4 | 0.60 - 0.94 | 1.58 | 0.013 - 0.019 | NA |
| S13 | M | 55 | yes | 113/77 - 118/70 | 78 - 93 | 18 | 0.67 - 1.01 | 1.51 | 0.017 - 0.021 | grafts patent |

S: Subject
BP (mm Hg): rest systolic/diastolic blood pressure - peak hyperemic systolic/diastolic blood pressure
HR (bpm) : rest heart rate - peak heart rate (bpm)
SSS: summed stress score (<4:normal; 4-8:mildly abnormal; 9-13:moderately abnormal; 13 severely abnormal)
K1 (mL/min/g): rest k1 - stress k1
CFR: coronary flow reserve (K1 stress / K1 rest)
K2 (1/min): rest k2 - stress k2
LAD: left anterior descending LCX: left circumflex artery RCA: right coronary artery

FIG. 7

FACTOR ANALYSIS IN MEDICAL IMAGING

CROSS-RELATED APPLICATION

This application is a divisional application of and claims priority under 35 U.S.C. §120 to U.S. Ser. No. 11/148,700, filed on Jun. 9, 2005, now U.S. Pat. No. 7,127,095 which claims priority under 35 U.S.C. 119(e)(1), of provisional application U.S. Ser. No. 60/682,173 filed May 17, 2005 and provisional application U.S. Ser. No. 60/619,296, filed Oct. 15, 2004.

TECHNICAL FIELD

This invention relates to medical imaging and more particularly to factor analysis.

BACKGROUND

Factor analysis of dynamic sequences ("factor analysis") is a powerful technique for the analysis of dynamic sequences. However, with factor analysis, different initial conditions can lead to different solutions. Several techniques have been developed that address this problem, and improve the results of factor analysis. Some of these techniques, in particular those based on the use of a priori physiological information, may be tailored for a particular type of clinical study. These techniques generally require modification when used in different settings. For example, a particular factor analysis approach might yield satisfactory results for studies of healthy people but might not work for studies of patients with different degrees of ischemia, different ejection fractions and, therefore, large differences in the shape and amplitude of blood flow time activity curves, also known as "activity curves" or "factors."

Other techniques address non-uniqueness of factor analysis solutions by minimizing a single objective function that penalizes the overlaps between factor images. Although these techniques increase the range of situations in which unique factor analysis solutions are achieved, in some situations they do not ensure a unique solution. For example, there are some situations where complete overlap of the resulting images of the factors, referred to herein as "factor images," can prevent uniqueness. This is, however, very unlikely in cardiac imaging as the left and right ventricles are spatially disjoint.

Some major challenges of factor analysis include improving spatial resolution of images, estimating activity curves from noisy data without arterial blood sampling, and assessing absolute myocardial blood flow and coronary flow reserve.

SUMMARY

In an aspect, the invention features methods and computer readable mediums for processing image data. The method includes estimating initial factor images from image data; transforming the estimated initial factor images by a transformation variable to obtain transformed factor images; providing an objective function that is a function of the transformed factor images; and minimizing the objective function to obtain unique factor images from the estimated initial factor images.

In some embodiments, initial factors are estimated from the image data; and a value of the transformation variable is determined such that the value minimizes the objective function; and unique factors are obtained using the value of the transformation variable and the estimated initial factors. In other embodiments estimating the initial factor images and factors include minimizing a least squares objective function, minimizing a penalized least squares objective function, or applying an apex seeking estimation technique.

In some embodiments, the transformation variable includes a rotation matrix and the objective function includes at least one penalty term that forces a condition on a solution based on a priori information such that minimizing the objective function minimizes the penalty term. For example, in some embodiments, minimizing the penalty terms penalizes overlap of the initial factor images and/or negative values of the initial factors and coefficients of the initial factor images.

In another aspect, the invention features methods and computer readable mediums for estimating kinetic parameters from image data. The method includes providing a model of kinetic contributions from first and second physiological regions; grouping voxels of the image data into first and second groups; determining an average value of the factors associated with the first group; incorporating the average value into the model; and estimating the kinetic parameters based on the model.

In some embodiments, the model is provided with input functions that include factors determined for the first and second physiological regions. In other embodiments, a vector space spanned by the voxels is reduced to a subspace within the vector space. In further embodiments, a first seed voxel, for which a sum of distances between the first seed voxel and other voxels of the image data is greatest, is determined and grouped with a first predefined number of ungrouped voxels that are located nearest to the first seed voxel. In some embodiments, a second seed voxel is determined and grouped with a second predefined number of remaining ungrouped voxels that are located nearest to the second seed voxel. In other embodiments, the first predefined number is selected to be equal to the second predefined number. In further embodiments, the first seed voxel is grouped with ungrouped voxels located within a minimum distance from the first seed voxel.

In some embodiments, the model is selected to be a two-compartment model of myocardial factors and of kinetic contributions from a left ventricle and a right ventricle; and estimating the kinetic parameters includes determining extraction and egress rates of transport between myocardial tissue and freely diffusible space.

In a further aspect, the invention features a medical imaging system that includes a data collection system; and a data processing system in communication with the data collection system. In some embodiments, the data collection system includes a PET system, a CT system, a SPECT system, an ultrasound system, or a fluoroscopy system.

Advantages that can be seen in particular implementations of the invention include one or more of the following. Robust estimates of activity curves and kinetic parameters may be obtained from image data without drawing volumes of interest (VOI). Activity curves and kinetic parameters may be estimated non-invasively without a priori knowledge of the image data. Activity curves may be estimated from variety of dynamic imaging applications. In some implementations, activity curves estimates are significantly more accurate and more robust to noise than activity curves estimates obtained using a volume-of-interest (VOI) based approach. Unique activity curves and factor image solutions and independent factor images of different physiological regions may be obtained. The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7 shows a table of clinical data for patients included in a study.

DETAILED DESCRIPTION

General factor analysis of dynamic sequences ("generalized factor analysis") and approaches based on generalized factor analysis enables the extraction of blood flow time activity curves ("activity curves") from noisy image data without arterial blood sampling. The extracted activity curves may be applied to a physiological model from which physiological parameters are determined. Examples of physiological parameters include absolute myocardial blood flow and coronary flow. Activity curves may also be referred to as "factors". The terms "activity curves" and "factors" are interchangeable.

Figure 1:
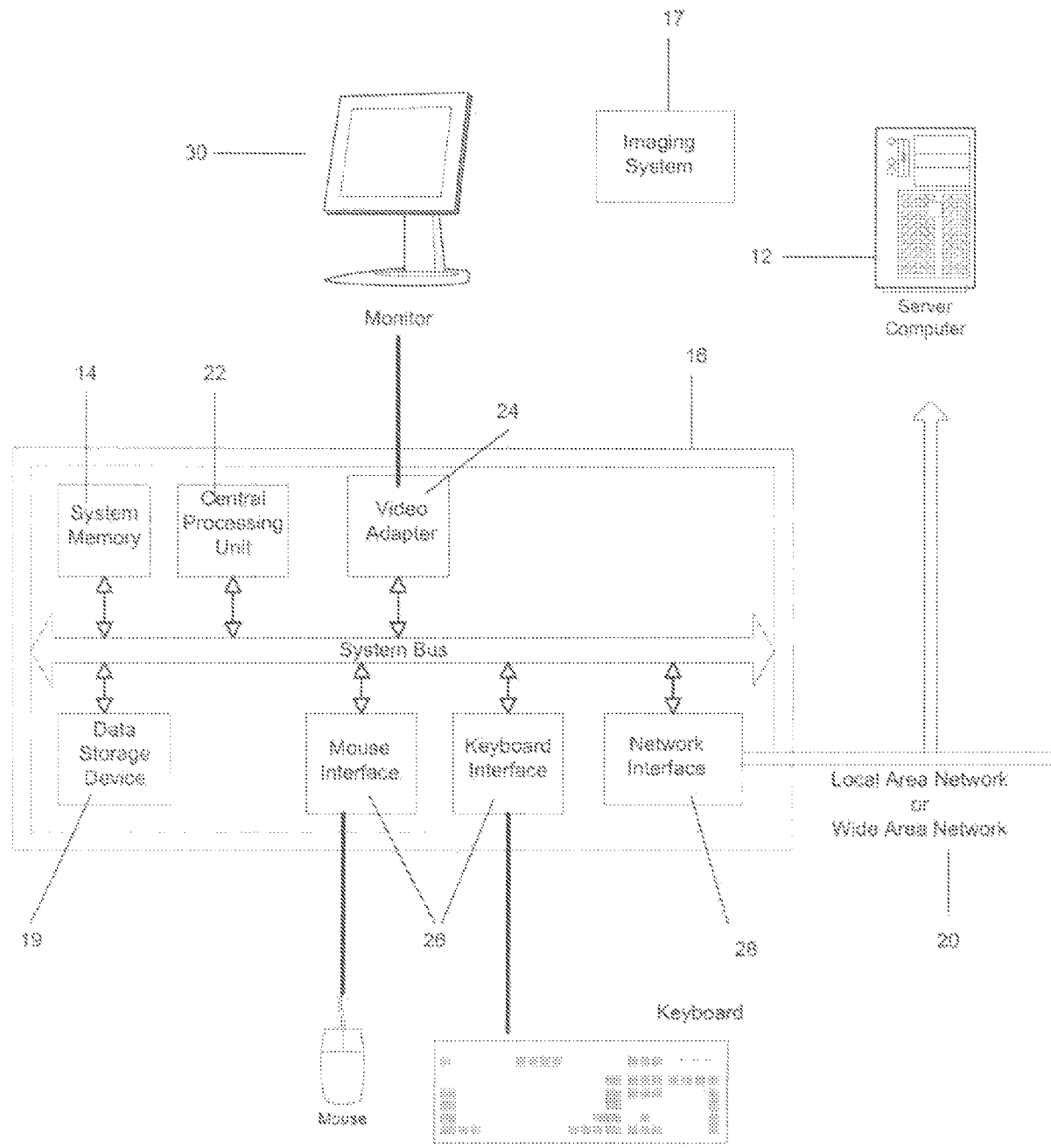
FIG. 1 shows a system for analyzing image data.

FIG. 1 shows an exemplary system 10 for analyzing image data using an approach based on generalized factor analysis. The system 10 includes a personal computer 16 for executing computer code; a monitor 30 for displaying data to a user; one or more input devices, such as keyboard and mouse, removable media 18 such as a floppy disk, CD-ROM, or other storage mechanism from which software is loaded into the personal computer 16; one or more server computers 12 for storing data collected from an imaging system 17, and a communications network 20 for sending data from the server computer 12 to the personal computer 16. In an exemplary embodiment, the imaging system 17 is connected to communications network 20 and configured to send data directly to the personal computer 16. Examples of an imaging system 17 include, but are not limited to, positron emission tomography (PET) imaging systems, computed tomography (CT) imaging systems, magnetic resonance imaging (MRI) systems, fluoroscopy imaging systems, ultrasound imaging systems, and single photon emission computed tomography (SPECT) imaging systems.

The personal computer 16 includes a data storage device 19, such as a hard drive, for storing data, system memory 14 for storing software, and a central processing unit 22 for executing the software stored in the system memory 14. The personal computer 16 also includes a video adapter 24 that interfaces the monitor 30, peripheral device interfaces, such as a mouse and keyboard interface 26, and a network interface 28.

In exemplary embodiments, the software supports a single user environment. For these embodiments, the communications network 20, the network interface 28, and the server computers 12 may be absent from the system 10. In other exemplary embodiments, the software supports multiple users collaborating on the development and use of activity curves-analysis techniques. In these embodiments, models and medical image data may be transmitted between multiple server computers 12 and personal computers 16 over a communications network 20. Examples of a communications network 20 include a local area network (LAN), a larger group of interconnected systems such as the internet, a private intranet, and other similar wired or wireless networks.

Figure 2:
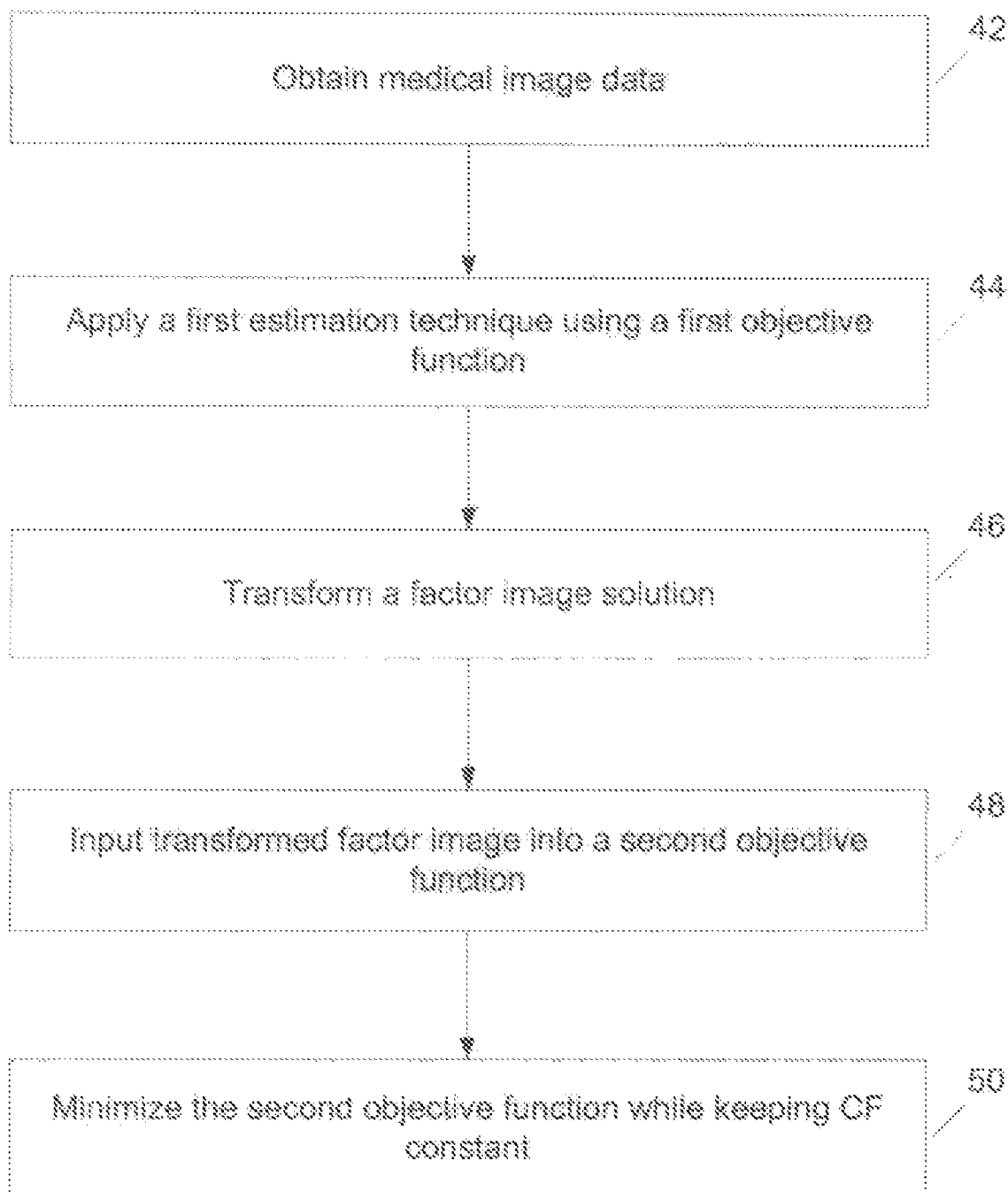
FIG. 2 shows a flow diagram of a generalized factor analysis process performed by the system shown in FIG. 1.

FIG. 2 shows a generalized factor analysis of dynamic sequences process 40 for analyzing image data. A dynamic sequence of medical images is obtained using an imaging technique (step 42). Examples of imaging techniques include, but are not limited to, positron emission tomography (PET), computed tomography (CT), magnetic resonance imaging (MRI), fluoroscopy, ultrasound imaging, and single photon emission computed tomography (SPECT). In some imaging techniques, a contrast agent is administered to the patient to improve the visibility of particular physiological features in the image data. In exemplary embodiments, PET is used to obtain the image data following administration of a contrast agent containing radioactive $^{82}$Rb to the patient.

The obtained medical images are represented by an N×M matrix A, where N is the number of voxels in an image and M is the number of time frames. The factor model of the dynamic data assumes that the data matrix can be represented by the following equation:

$$A = CF + n,\qquad\text{Eq. 1}$$

where, the factor matrix F is a P×N matrix of P factors, the factor image matrix C is an N×P matrix of factor images, and n denotes noise in the data. The factor curves define the time course of a given factor whose spatial definition is contained in the factor image matrix C. As a result, the structures shown in a factor image are assumed to have the same or similar temporal behavior. To solve Equation 1, the number of factors P must be known a priori. In exemplary embodiments, P is chosen to be equal to three. This provides two rows for factors that represent the blood activity in the left and right ventricles, and one row for the factor representing activity in the myocardial tissue.

The factor matrix (F) and factor image matrix (C) are estimated using a first estimation technique (step 44). In some exemplary embodiments, estimation of the factor matrix (F) and factor image matrix (C) is based on minimization of the least squares objective function $f_{LS}$, which minimizes a least square error:

$$f_{LS}(C, F) = \sum_{i=1}^{N}\sum_{m=1}^{M}(A_{im} - \sum_{p=1}^{P}C_{ip}F_{pm})^2.\qquad\text{Eq. 2}$$

Examples of additional estimation techniques include, but are not limited to, targeted apex seeking estimation, and penalized least squares estimation in which the least squares objective function (shown in Equation 2) is modified by adding terms that penalize negative and/or non-unique values of C and F. Examples of penalized least squares estimation are described in U.S. Patent Publication Ser. No. 2003/0048937 by Gullberg et al. Because the factor model described by Equation 1 is not mathematically unique, the solutions obtained for F and C using the least squares estimation technique of Equation 2 may not be unique (i.e., there is no guarantee that the same solution will be reached with different initial conditions). Non-unique solutions for F and C appear as overlapping physiological regions within a factor image. By contrast, unique solutions for F and C result in only one physiological region being present in a factor image.

To increase the likelihood of obtaining unique solutions for F and C, a post-processing method is used to modify the factors and factor images obtained in the initial estimation procedure (step 44). The post processing procedure provides unique solutions for the factors and factor image estimates obtained from the initial estimation procedure (step 44). The initial estimates of factor and factor image matrices (F and C, respectively) are transformed by a rotation matrix R (step 46) and entered into a second objective function (step 48). The transformed factor and factor image matrices, C' and F', are given by $C'=CR$ and $F'=R^{-1}F$. The second objective function, $f_{ob}(R)$, is a function of R and is equal to the sum of a non-uniqueness penalty function $f_{uni}(R)$ and a negativity penalty function $f_n(R)$ weighted by a penalty parameter, b, that adjusts the strength of the negativity penalty function:

$$f_{ob}(R)=f_{uni}(R)+bf_n(R).\qquad\text{Eq. 3}$$

The non-uniqueness penalty term, $f_{uni}(R)$, which penalizes the overlap between factor images, is expressed as:

$$f_{uni}(R)=\sum_{p=1}^{P}\sum_{q=p+1}^{P}\sum_{i=1}^{N}\frac{|CR_{ip}|}{\sqrt{\sum_{j=1}^{N}CR_{jp}^2}}\frac{|CR_{iq}|}{\sqrt{\sum_{j=1}^{N}CR_{jq}^2}}.\qquad\text{Eq. 4}$$

Image overlap results from non-unique solutions; therefore, penalizing the overlap between factor images increases the likelihood that a unique solution is obtained.

The negativity penalty function $f_n(R)$, which imposes negativity constraints on the objective function, is given by:

$$f_n(R)=\sum_{i=1}^{N}\sum_{p=1}^{P}H(CR_{ip})+\sum_{p=1}^{P}\sum_{m=1}^{M}H(R^{-1}F_{pm}),\qquad\text{Eq. 5}$$

where:

$$H(X)=\begin{cases}0&\text{for }x\geq 0\\ x^2&\text{for }x<0.\end{cases}\qquad\text{Eq. 6}$$

The negativity penalty function $f_n(R)$ penalizes negative values of the transformed factor image and factor matrices C' and F'. Negative values of C' and F' are not physiologically meaningful; therefore, the negativity penalty function ensures that the solutions for C' and F' are positive.

The second objective function, $f_{ob}(R)$, is then minimized while keeping the product of C and F constant (step 50). The value of the rotation matrix R that minimizes the objective function is determined. This value is referred to as $R_{min}$. The results of the minimization are unique factor and factor image matrices, F' and C', which are expressed as $F'=R_{min}^{-1}F$ and $C'=CR_{min}$, where $R_{min}$ is the rotation matrix determined during the minimization of the objective function. In some exemplary embodiments, the objective function is minimized using a simplex algorithm. In some of these embodiments, convergence is reached after approximately 100 to 500 iterations. In additional exemplary embodiments, the value of the penalty parameter, b, is not critical for the convergence to a solution when that value is chosen in a range approximately between 0.05 and 0.5. The C and F solutions obtained in the first estimation procedure (step 44) hold after the minimization procedure (step 48) such that:

$$C'F'=(CR)(R^{-1}F)=CF.\qquad\text{Eq. 7}$$

In other words, F' and C' are the unique solutions that belong to the set of non-unique solutions obtained in the first estimation procedure (step 44).

Depending on the application and physiology of the imaged tissue, the second objective function may include any combination of penalty terms that force one or more conditions on the solution for C' and F'. In some exemplary embodiments, the second objective function contains additional penalty functions to force other conditions on the solutions. Examples of conditions include non-zero conditions, and other conditions that may be produced using a priori information about the data such as stationarity, or any particular time varying function of the activity curves. In additional embodiments, instead of penalizing overlap between factor images, the non-uniqueness penalty term minimizes a different effect of non-uniqueness, such as the entropy of factors. Examples of using entropy of factors to minimize non-uniqueness may be found in the paper by A. Sitek, E. V. Di Bella, and G. T. Gullberg, "Factor Analysis of Dynamic Structures in Dynamic SPECT Imaging Using Maximum Entropy," IEEE Trans Nucl Sci, vol. 46, pp. 2227-2232, 1999).

By minimizing a major effect of non-uniqueness, namely overlap between factor images, generalized factor analysis obtains unique solutions for the factor images and their corresponding factors.

Figure 3:
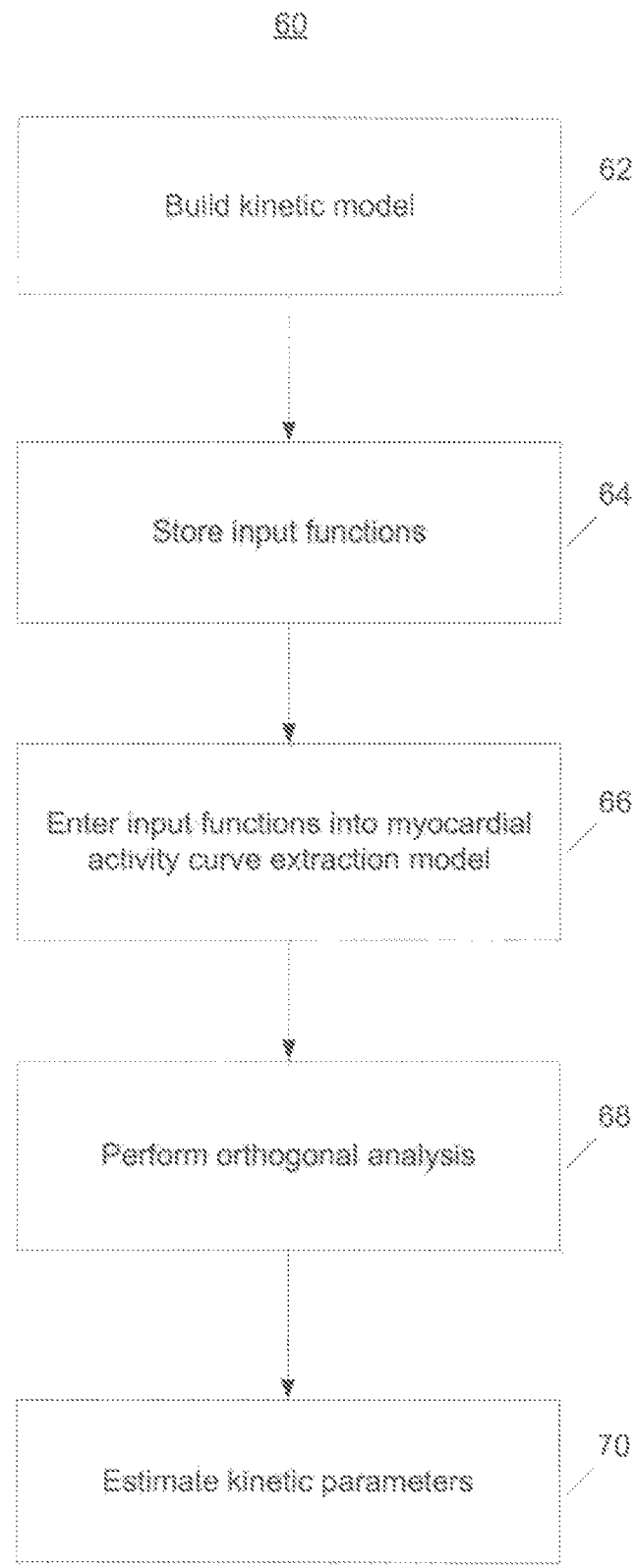
FIG. 3 shows a flow diagram of a compartmental analysis process for estimating blood flow parameters using input functions obtained by the generalized factor analysis process shown in FIG. 2.

FIG. 3 shows a process 60 for estimating blood flow parameters using a kinetic model of myocardial activity curves. Because some tracers, such as $^{82}$Rb, are only partially extracted by the myocardium, a two-compartment model is used to estimate myocardial activity curves. The two-compartment model includes a "free rubidium space" (blood perfusing the myocardium and the interstitial space) and a "trapped rubidium space" (muscle of the myocardium). The blood flow parameters of the model include kinetic transport constants $k_1$ (ml/min/g) and $k_2$ (min$^{-1}$), which, respectively, represent extraction (forward) and egress (backward) rates of transport between metabolically trapped space (myocardium) and freely diffusible space (blood pool).

A general kinetic model of the myocardial activity curves of a voxel is built from the two-compartment model (step 62). In the kinetic model, the myocardial activity curves in each voxel are modeled as a combination of three contributions: the contribution from the myocardial tissue, which is modeled using the two-compartment model, and the contributions from the left and right ventricular cavities, which are modeled as fractions of measured LV and RV functions. In cardiac imaging it is useful to explicitly model the contribution from the RV in order to obtain stable and robust voxel parameter estimates. The two-compartment kinetic model is expressed as:

$$TAC_i(t)=I(t)\otimes k_1^i\exp(-k_2^i t)+f_v^i I(t)+r_v^i R(t),\qquad\text{Eq. 8}$$

where $TAC_i(t)$ are the myocardial activity curves of a voxel i at time t, I(t) is the input function (i.e., measured LV function), "$\otimes$" is a convolution operator, and $k_1^i$ and $k_2^i$ are the myocardial extraction (inflow) and egress (outflow) kinetic parameters for voxel i. Absolute myocardial blood flow and coronary flow reserve may be determined using the $k_1^i$ and $k_2^i$ kinetic parameters. The remaining two terms in Equation 8 represent the weighted contributions to the total voxel activity from the LV blood input function I(t) and from the activity in the RV, R(t). The values of $f_v^i$ and $r_v^i$ are the weighting coefficients corresponding to these contributions. The parameters $k_1^i$, $k_2^i$, $f_v^i$, $r_v^i$, may be zero-valued for some voxels. A voxel of a myocardium image may contain a mixture of the LV, RV, and myocardium. Therefore, the two-compartment kinetic model expresses the myocardial activity curves of a voxel as a sum of the contributions of the LV and RV activity curves and the LV blood input function I(t) convolved with an exponential function that depends on the myocardial tissue extraction and egress kinetic parameters.

The two-compartment kinetic model receives LV and RV activity-curve input functions, referred to as I(t) and R(t), respectively. The input functions I(t) and R(t) are the unique LV and RV factors F' determined using the generalized factor analysis process 40 described in FIG. 2; however, the input functions may be determined using other approaches as well. For example, in some exemplary embodiments, the input functions are determined using volume-of-interest (VOI) analyses. In a VOI analysis, a skilled operator defines a VOI over a three-dimensional volume obtained from several frames of medical images. Activity curves for the VOI are generated by estimating counts within the VOI defined for each frame. In additional exemplary embodiments, Monte Carlo simulations are used for estimating the input functions based on a VOI. In further exemplary embodiments, the VOI for each slice is first reduced, for example by 50%, to minimize overlap between LV, RV and myocardial images. After the input functions, I(t), R(t), and $TAC_i(t)$ are obtained, they are stored in memory (step 64) and entered into the kinetic model (step 66).

The estimation of parametric images on a voxel-by-voxel basis can yield noisy images due to high levels of noise in the activity curves derived from single voxels. Traditional approaches to this problem involve filtering or clustering to reduce the noise. These approaches, however, degrade the spatial resolution of the parametric images.

To reduce noise and preserve spatial resolution, an orthogonal grouping procedure is performed on the voxels (step 68). In this procedure, voxels with similar myocardium activity curves are grouped together and average activity curves for each group of voxels are determined. The noise level of the average activity curves is generally much less than the noise level of activity curves derived from single voxels. The two-compartment kinetic model (expressed in Equation 8) is applied to the voxel groupings rather than to the individual voxels. Input functions for several time points are entered into Equation 8 to produce a uniquely solvable set of equations for the average myocardial activity curves of a voxel grouping. Solving the set of equations yields estimates for the parameters $k_1^i$, $k_2^i$, $f_v^i$, and $r_v^i$ for each voxel grouping i (step 70). The parameters determined for a voxel grouping are assigned to the voxels belonging to that voxel grouping.

Figure 4:
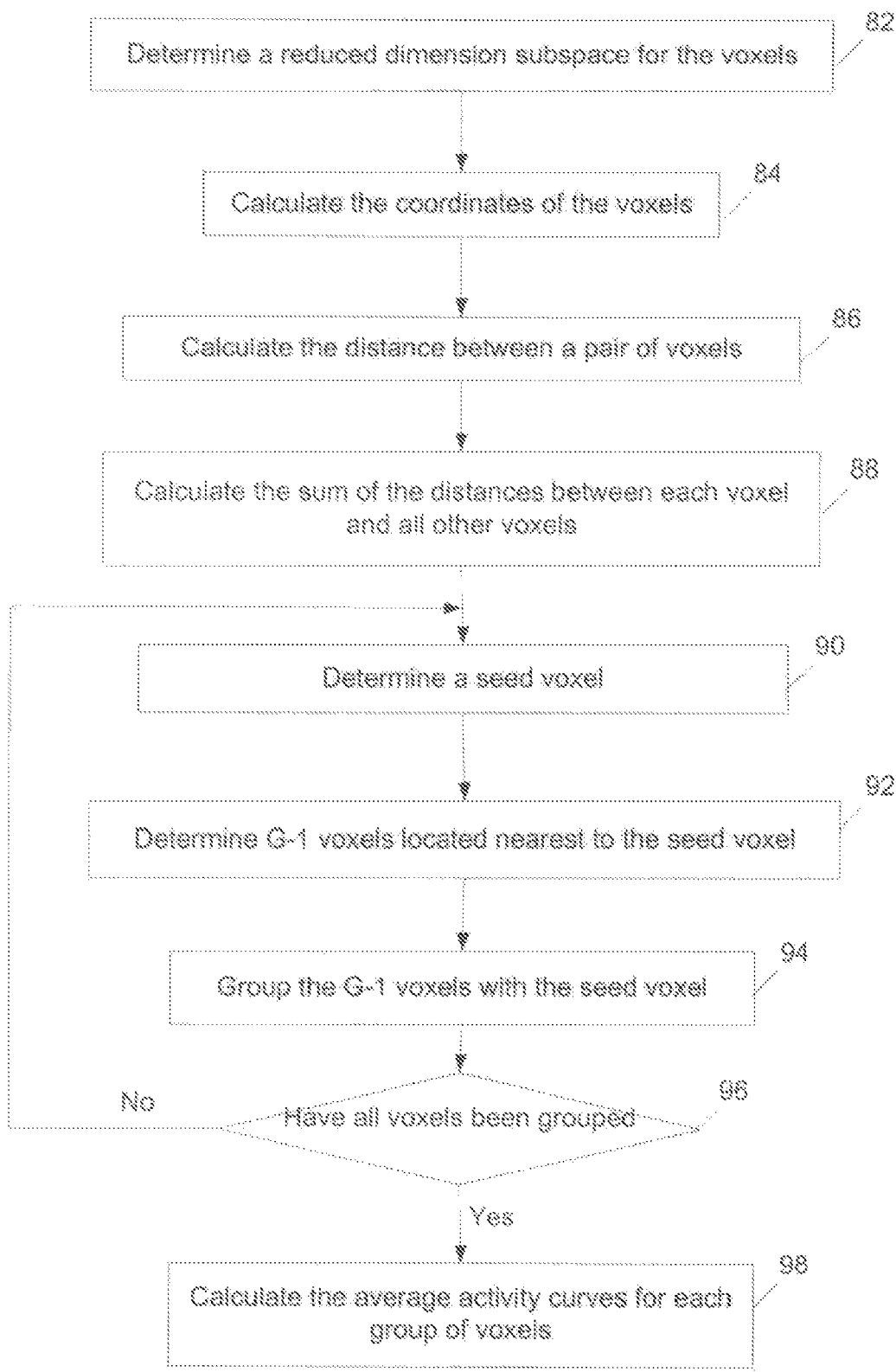
FIG. 4 shows a flow diagram of an orthogonal grouping process for use with the compartmental analysis process shown in FIG. 3.

FIG. 4 shows the orthogonal grouping procedure (step 68) of process 60 in further detail. In the orthogonal grouping procedure, voxels having similar myocardium activity curves are grouped together into groups of size G, where G denotes the number of voxels in a group.

Orthogonal grouping (step 68) includes an orthogonal analysis step (step 82) in which the vector space spanned by the basis vectors associated with the voxels is reduced to a subspace S that contains most of the data associated with the voxels. The subspace S includes the space spanned by principal vectors of the voxels. A principle vector V is an eigenvector such that for a given matrix M, $MV=\lambda V$ where $\lambda$ is a singular value associated with the principle vector V. For example, a twenty-dimensional vector associated with a voxel may be modified to span only three dimensions. In an exemplary embodiment, the subspace S is determined by setting small singular values of the vector space of the voxels to zero. The principal vectors spanning subspace S may not correspond to physiological tissue curves, and some of the principal vectors may have negative values.

The coordinates of each voxel i in the reduced-dimensional subspace S are calculated as the product of the principal vectors with $TAC_i(t)$ (step 84). For example, if subspace S is three-dimensional, the coordinates of voxel i are represented as three-dimensional vectors $P(TAC_i(t))_\tau$, where $\tau=1 \ldots 3$, and P denotes the projection operator onto the $\tau^{th}$ principal vector. The resulting $P(TACi(t))\tau$ vectors described the location of a given dynamic voxel $TAC_i(t)$ in the three-dimensional sub-space S.

A grouping algorithm is then applied to the three-dimensional vectors $P(TAC_i(t))_\tau$. Cartesian distances $d_{ij}=\|P(TAC_i(t))_\tau - P(TAC_j(t))_\tau\|$ are calculated between each pair of voxels i and j (step 86). The sum of the distances between each voxel and all other voxels is calculated (step 88). A voxel for which the sum of the distances to all other voxels is greatest is determined (step 90). For ease of explanation, this voxel will be referred to as the "seed voxel." Next, the G−1 dynamic voxels that are located nearest to the seed voxel are determined (step 92). The G−1 dynamic voxels and the seed voxel (G voxels total) are then grouped together (step 94). The orthogonal grouping process (step 68) determines whether all of the voxels have been grouped (step 96). If ungrouped voxels remain, the determining processes (steps 90 and 92), and the grouping process (step 94) are repeated for the remaining voxels until all of the voxels are grouped. The number of voxels in a group, G, is chosen iteratively to be the smallest value that would ensure convergence for all groups. The average activity curves for each group are calculated and entered into the two-compartment kinetic model, described in Equation 8 (step 98).

Increasing G generally reduces the noise in the average activity curves. In some embodiments, the value of G is determined heuristically such that the level of noise of the average activity curves of a voxel grouping is at or below a predetermined threshold. For example, the determining processes (steps 92 and 96), the grouping process (step 94), and the calculating process (step 98) may be performed iteratively with different values of G until an acceptable value or range of values for G is found. In exemplary embodiments, Monte Carlo simulations are used to determine G. In some of these embodiments, G is approximately 30. In additional exemplary embodiments, patient studies are used to determine G. In some of these embodiments, G is approximately 30.

Alternatively, different grouping algorithms may be used to group the voxels. For example, in some embodiments, after a seed voxel is determined (step 90), the voxels located within a minimum distance from the seed voxel are determined and grouped together with the seed voxel. In these embodiments, G may vary from group to group. Furthermore, in some embodiments, the grouping algorithm ensures that G is greater than a predefined threshold (e.g., G is greater than 10 voxels). In additional embodiments, the grouping algorithm ensures that G is less than a predefined threshold (e.g., G is less than 100 voxels). In further embodiments, the grouping algorithm ensures that G lies within a predefined range (e.g., G is greater than 10 voxels but less than 100 voxels).

EXAMPLES

Monte Carlo Simulations of Dynamic $^{82}$Rb-PET Studies

The performance of the generalized factor analysis process (FIG. 2) and the compartmental analysis process (FIG. 3) were tested using Monte Carlo simulations. Dynamic $^{82}$Rb cardiac PET was used to measure the LV and RV activity curves in ten human patients while the patients were at rest and while the patients were subjected to dipyridamole-stress.

The measurements were taken from small volumes of interest positioned over the patients' LV and RV cavities. The patients were imaged at different time-points in the life of the $^{82}$Rb generator. Of the ten patients, there were six without evidence of obstructive coronary artery disease (CAD) as determined by the absence of regional perfusion defects on the dipyridamole-stress images. A summed stress score (SSS) of zero was assigned to these images to indicate the absence of regional perfusion defects. In addition, there were four patients with known obstructive CAD and extensive perfusion abnormalities on the dipyridamole-stress images. An SSS score for these images was greater than eighteen. The LV and RV activity curves obtained from the patients varied in shape and represented a wide range of physiologic conditions.

Because $^{82}$Rb is a partially extracted tracer, the myocardial activity detected in a small region is the sum of the activity trapped in the cell and the free circulating activity. When modeling the myocardial uptake, the myocardial tissue contained approximately 25% of arterial blood (i.e., 25% of the radioactive uptake in the myocardium is arterial blood and 75% is myocardial tissue). The LV activity curve, I(t), was used as an input function for a two-compartment kinetic model in order to generate pure myocardial extraction fraction (extra vascular space) activity curves:

$$TAC(t) = k_1 \int_{\tau=0}^{t} I(t-\tau)e^{-k_2\tau}d\tau. \quad \text{Eq. 9}$$

Figure 5:
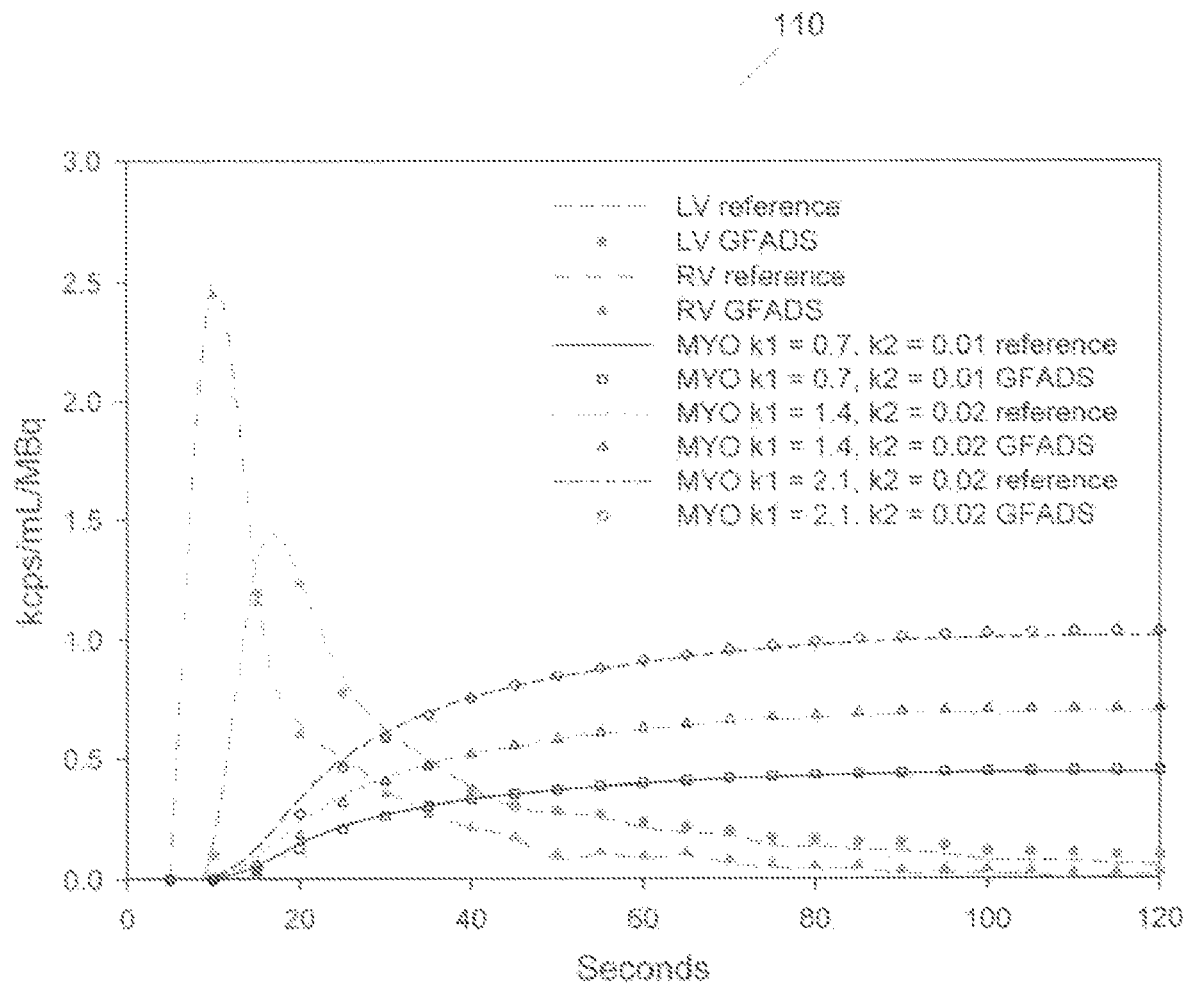
FIG. 5 shows a plot of simulated activity curves from the right ventricle (RV), left ventricle (LV), and myocardium and corresponding activity curves estimated by the generalized factor analysis process shown in FIG. 2.

Myocardial extraction activity curves were generated for rest studies with $k_1$ values of 0.4, 0.7 and 1.2 ml/min/g and for stress studies with $k_1$ values of approximately 0.7, 1.4 and 2.1 ml/min/g. Because $^{82}$Rb is an analogue of potassium, which is taken up rapidly and retained for a long time within myocardial cells, very low $k_2$ values of approximately 0.01 and 0.02 min$^{-1}$ were used in rest and stress studies. The selected values of $k_1$ and $k_2$ spanned the range of values reported in the literature in rest and stress studies. The lowest two $k_1$ values were associated with $k_2=0.01$ min$^{-1}$, while the highest $k_1$ value was associated with $k_2=0.02$ min$^{-1}$. Typical myocardial activity curves obtained using our kinetic model were compared to those measured using small myocardial VOI in patients, and several were found to match patient activity curves quite well. Since three pairs of ($k_1$, $k_2$) values were used with 10 pairs of (LV, RV) input functions, a set of thirty unique realistic simulated dynamic studies was obtained. Sample LV and RV input functions, as well as three myocardial activity curves, are shown in FIG. 5. The reference RV, LV, and myocardial activity curves (shown as solid and dashed lines) represent the true activity curves for the RV, LV, and myocardium while the open symbols represent the corresponding factors estimated using the generalized factor analysis approach. The activity curves obtained using the generalized factor analysis approach show very strong agreement with the reference activity curves.

In other studies, an anthropomorphic Zubal torso phantom was used. The heart was segmented into LV and RV cavities, myocardial muscle, and blood pool, all of which were assumed to have uniform activity distributions. 2D PET Monte Carlo simulations of the LV and RV, as well as the myocardium and other organs (e.g., liver, soft tissue, etc.), were performed separately and combined to generate 30 realistic dynamic $^{82}$Rb studies using the activity curves obtained using the generalized factor analysis method (step 60).

A 2D PET scanner was modeled to be similar to a GE DST discovery PET/CT scanner (provided by General Electric Medical Systems, Milwakee, Wis.) with a uniform 3 cm thick bismuth germinate (BGO) detector (energy resolution=20% at 511 keV, axial extent=15 cm, ring diameter=88 cm). A stack of annular septa (septal thickness=0.1 cm) was explicitly modeled in the Monte Carlo simulation in the axial direction, yielding twenty-eight 3.3 mm-thick slices (voxel size was 3.3×3.3×3.3 mm$^3$). Events reaching the detector were binned into 128 projections using only the direct planes. Nine orders of Compton scatter were modeled. Positron range was also modeled using an analytical approach that used beta-decay energy spectra and empirical range formulas. Random coincidences were also modeled in the simulation. Random coincidences were estimated from singles using:

$$R_{random} = CTW \times R_{single,1} \times R_{single,2} \quad \text{Eq. 10}$$

where CTW is the coincidence timing window (12 nsec), and $R_{single,1}$ and $R_{single,2}$ are the single-channel counting rates in the two detectors of the detector pair. Singles were simulated by tracking single 511-keV photons (e.g., rather than photon pairs) using the same activity and attenuation distributions as those used in the actual PET simulation. Twice as many decays were generated for the singles simulation than for the PET simulation because one decay yields two annihilation photons. Variance reduction techniques, including stratification and forced detection, were used when tracking photons.

Approximately nine billion photons were generated while simulating the LV, RV, myocardium, and soft tissues. The simulations yielded essentially noise-free sinograms which were used as the basis for generating noisy sinograms with a Poisson multiplicative congruential pseudo-random generator. Next, the scatter, which was known from simulation, random coincidences, and estimates derived the singles-rate formula (Equation 10), were subtracted from the sinograms. The resulting sinograms were pre-corrected for attenuation by multiplying each ray-sum by the inverse of the corresponding attenuation factor. The result was reconstructed using ordered subsets expectation maximization (OSEM, 5 iterations, 4 subsets). Stationary resolution was assumed in the forward projector and no post-filtering was performed. This yielded thirty studies, each consisting of twenty-four 5-second frames (128×128×128 voxels each).

Dynamic $^{82}$Rb patient studies

Another study was performed on thirteen patients. Five of the patients had evidence of obstructive CAD while the other eight patients had no evidence of CAD. FIG. 7 shows a table 122 of the clinical data and calculated rest and stress myocardial blood flows for the patients.

Rest and stress dynamic protocols were performed in eight subjects, while rest dynamic data was available in four subjects and stress dynamic data in one subject. Patients undergoing the rest-stress protocol were injected with a bolus of 2.2±0.19 GBq (60±5 mCi of $^{82}$Rb) in 14±6 mL of saline and imaged dynamically for 6 minutes at rest and, ten minutes later, during dipyridamole stress (IV infusion of 0.14 mg/kg/min) for 4 minutes. The dynamic imaging protocol consisted of twenty-four 5-second frames ("fast frames") followed by eight 30-second frames. The initial fast frames were used to capture the rapid wash-in and wash-out of $^{82}$Rb from the left and right ventricular cavities.

Sinograms were acquired in 2D mode on a GE DST discovery PET/CT scanner with BGO detectors provided by GE Medical Systems, Milwakee, Wis. A CT scan was also performed with each PET study (70 mAs, 140 KVp) using an 8-slice helical scanner and shallow breathing (helical thickness=3.75 mm; pitch=1.35:1; 27 mm/rotation). The attenuation map used for correction of the 511 keV photon attenuation was derived from the CT scan using a continuous conversion scale with a range of slopes dependent on the CT kV and the CT number. Random correction was performed by direct subtraction of delayed events, and scatter correction was performed using the scatter modeling approach. All dynamic sinograms were reconstructed using the attenuation weighted-OSEM (AWOSEM) (21 subsets, 2 iterations, as recommended by the manufacturer) into twenty-four 5-second and eight 30-second frames, each being a 128×128×47 volume. No post-filtering was performed. Next, LV and RV input functions were computed using generalized factor analysis, and the two-compartment analysis was carried out, yielding voxel-by-voxel parametric maps. To avoid introducing inaccuracies arising from the short half-life for a 5 second frame, no decay correction was performed. The $k_1$ parameter, unlike the $k_2$ parameter, is not affected by radioactive decay.

Data Analysis

Estimation performance was assessed for the Monte Carlo-simulated data by computing known true values. The LV and RV activity curves estimated with generalized factor analysis or by VOI analysis were compared to the LV and RV input functions used to generate the dynamic studies. Likewise, the myocardial activity curves estimated with generalized factor analysis and VOI analysis were compared to the true myocardial time activity curves. For a given Monte Carlo simulation, the total generalized factor analysis (or VOI analysis) estimation error $\epsilon^{GFADS}$ of the LV, RV or myocardial activity curves was computed over the 24 time frames, and the average error over the 30 Monte Carlo studies expressed as:

$$E = \frac{1}{30}\sum_{k=1}^{30} \varepsilon_k^{GFADS} = \frac{1}{30}\sum_{k=1}^{30}\sum_{i=1}^{24}\left|1 - \frac{TAC_i^{GFADS}}{TAC_i^{Truth}}\right|_k.$$ Eq. 11

The standard deviation of the average error was also calculated over the 30 Monte Carlo after averaging over the time frames. Likewise, the average errors associated with myocardial tissue extraction ($k_1$) and egress ($k_2$), as well as RV and LV contributions ($f^i_v, r^i_v$), were computed over the 30 Monte Carlo simulations. The rate constants $k_1$, $k_2$, as well as $f^i_v$ and $r^i_v$, were averaged over each tissue compartment using the known simulated activity distribution as a mask. Errors were calculated using the known parameters' values used to generate the dynamic studies. Means and standard deviations of the errors were calculated over the 30 patients.

Results

FIG. 5 shows a plot 110 of the LV and RV input functions and myocardial activity curves that were assumed for the simulations, as well as the corresponding curves estimated using generalized factor analysis. Generalized factor analysis yielded accurate estimates of all three factors modeled in the Monte Carlo simulations, as well as the corresponding factor images, with average errors of −4.2±6.3%, 3.5±4.3% and 2.0±5.5% respectively, in the LV, RV and myocardial factor estimates. Errors were calculated with respect to the true factors used in the simulation over all time frames.

Figure 6:
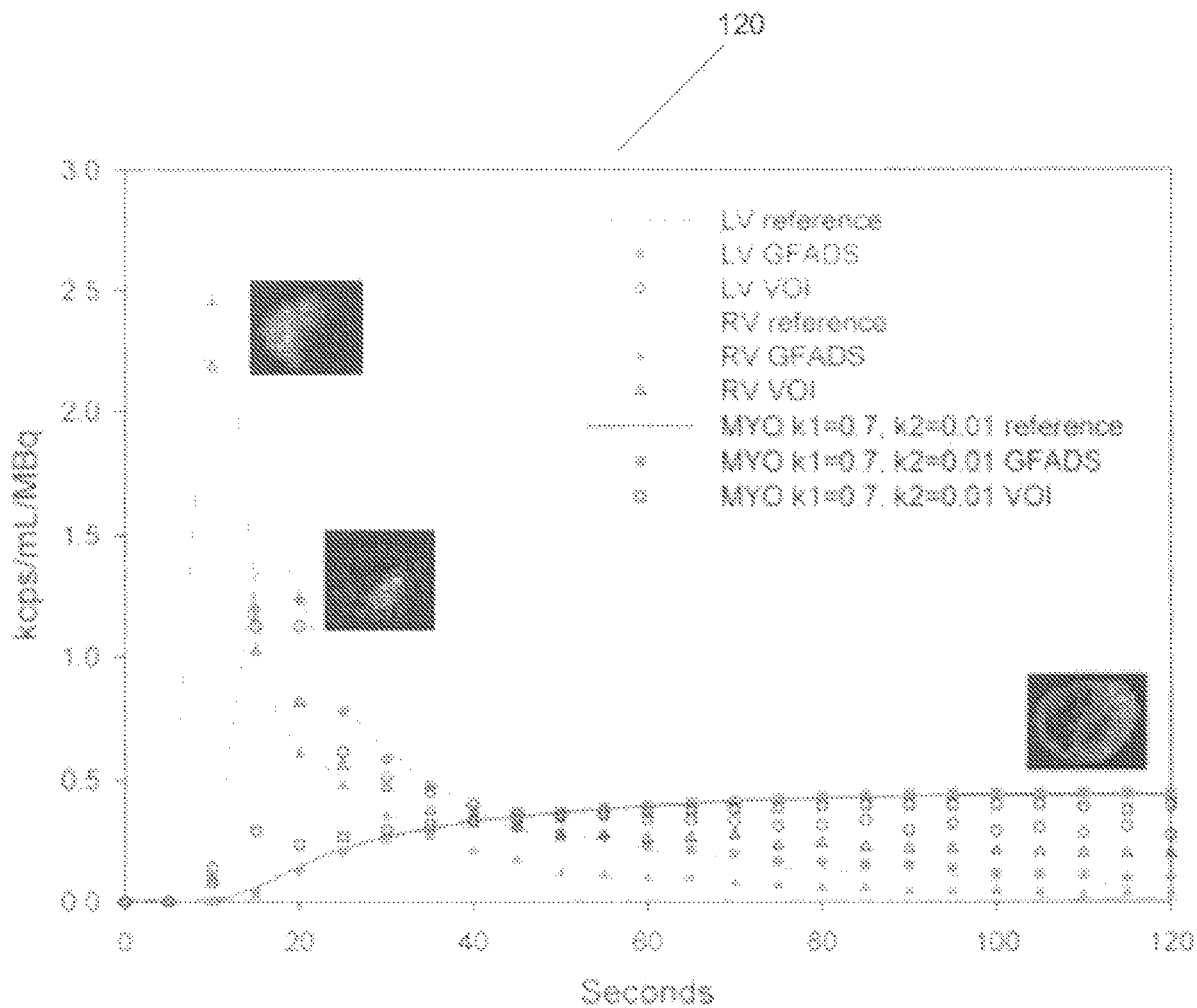
FIG. 6 shows a plot of simulated activity curves derived from a volume of interest approach and from the generalized factor analysis process shown in FIG. 2.

FIG. 6 shows a plot 120 of the simulated LV and RV input functions and the myocardial activity curves, as well as the corresponding factors, estimated by generalized factor analysis and by a VOI approach. Average errors were significantly higher with the VOI approach than with generalized factor analysis. The average errors of LV, RV and myocardial factor estimates obtained using activity curves based on manually drawn volumes of interest were significantly (p<0.001, paired t-test) higher at 30.7±8.3%, 26.5±6.2% and 7.3±7.1%, respectively. A single transverse image from the factor image corresponding to each factor is also shown. The activity curves derived from the VOI approach underestimates values of the true LV and RV input functions at early time points and overestimates values of the LV and RV input functions at later time points. The activity curves derived from the VOI approach also overestimate the myocardial activity curves at the early time points. This overestimation results from spillover of counts from the LV compartment into the myocardial compartment. This spillover is not observed with generalized factor analysis.

The two-compartment model kinetic analysis also yielded estimates of $k_1$, $k_2$, $f_v$ and $r_v$ parametric maps. The error in estimating the value of $k_1$, averaged over the myocardium, was approximately 6.8±3.6%. This error was slightly greater for $k_2$ (8.4±7.6%), as the simulated $k_2$ values were very low (i.e., between 0.01 and 0.02) and hence more sensitive to noise. Errors in the estimates of $f^i_v$ and $r^i_v$ were 6.5±2.8% and 7.3±2.7%, respectively. The corresponding errors when using activity-curve input functions estimated by VOI analysis were 28.6±7.9%, 11.3±6.3%, 45.7±7.8%, and 29.7±6.0% for $k_1$, $k_2$, $f^i_v$, and $r^i_v$, respectively.

In another study, the factors obtained using generalized factor analysis were used as inputs to a non-linear Lovenberg-Marquardt fitting procedure to estimate myocardial tissue extraction ($k_1$) and egress ($k_2$). Since $k_2$ was very small (<0.02 min$^{-1}$), values of the parameter $k_1$ were remapped back to the original images using the myocardial image of factor coefficients, thus yielding the parametric $k_1$ image as a quantitative measure of myocardial blood flow. The parametric images yielded estimates of $k_1$ and $k_2$, with average errors of 8.74±8.65% and 10.34±14.26%.

Patient clinical data at rest and stress, as well as the summed stress score and coronary flow reserve, are shown in the table 122 of FIG. 7. In all patient studies, generalized factor analysis yielded LV and RV input functions, myocardial activity curves, and corresponding factor images of the expected form.

Figure 8:
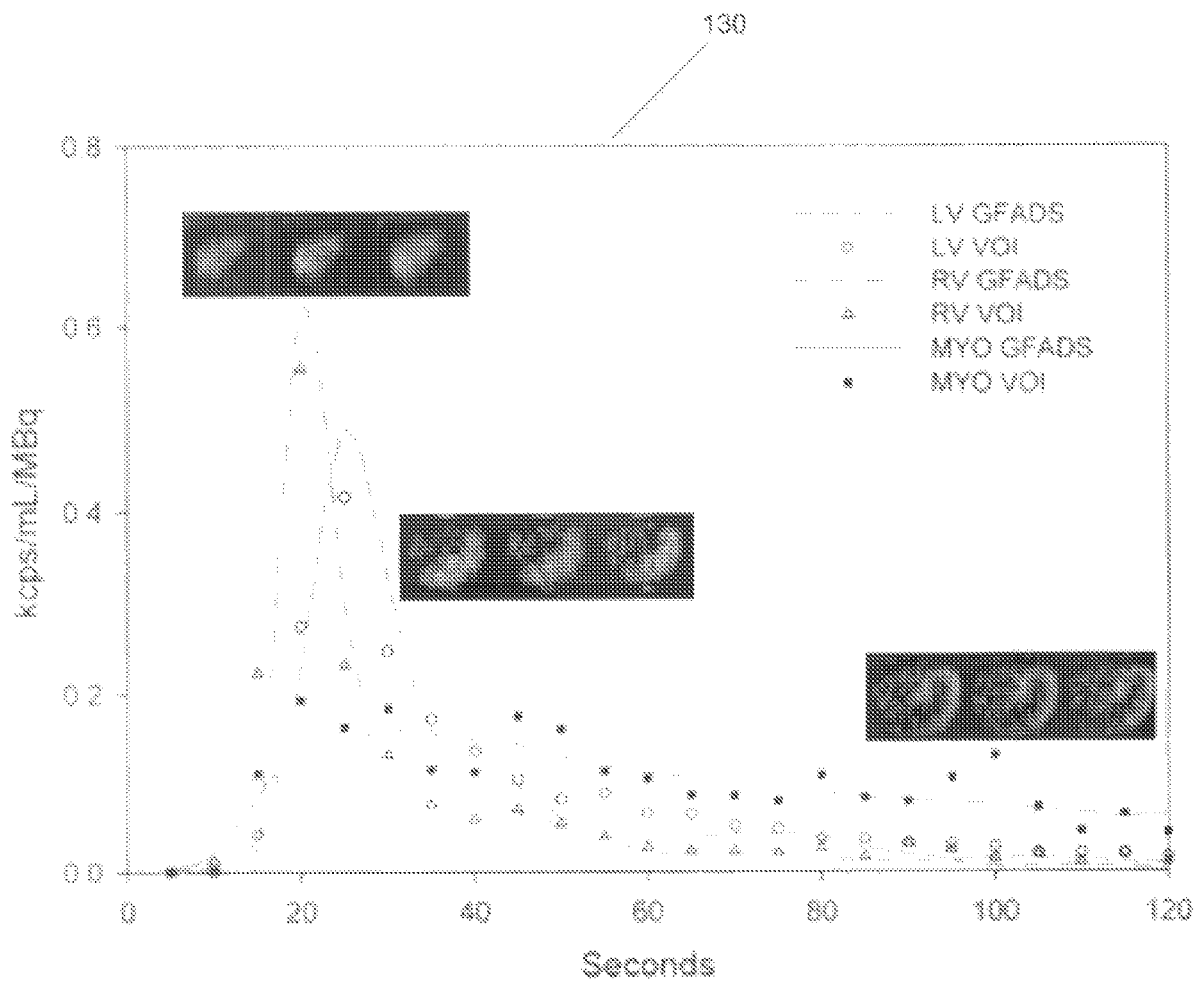
FIG. 8 shows a plot of estimated activity curves obtained using the generalized factor analysis process shown in FIG. 2 for a dynamic $^{82}$Rb PET study using the clinical data shown in FIG. 7.

FIG. 8 shows a plot 130 of estimated factors and factor images with generalized factor analysis for a typical dynamic $^{82}$Rb PET patient study. The patient had known CAD and normal myocardial perfusion (SSS=0). As seen in the images, the LV, RV, and myocardium obtained using generalized factor analysis were well separated, indicating unique factor and factor image solutions. Furthermore, the two-compartment kinetic model yielded parametric maps of myocardial tissue extraction and egress, as well as spill-over fractions from the blood pool into the myocardial tissue.

Figure 9:
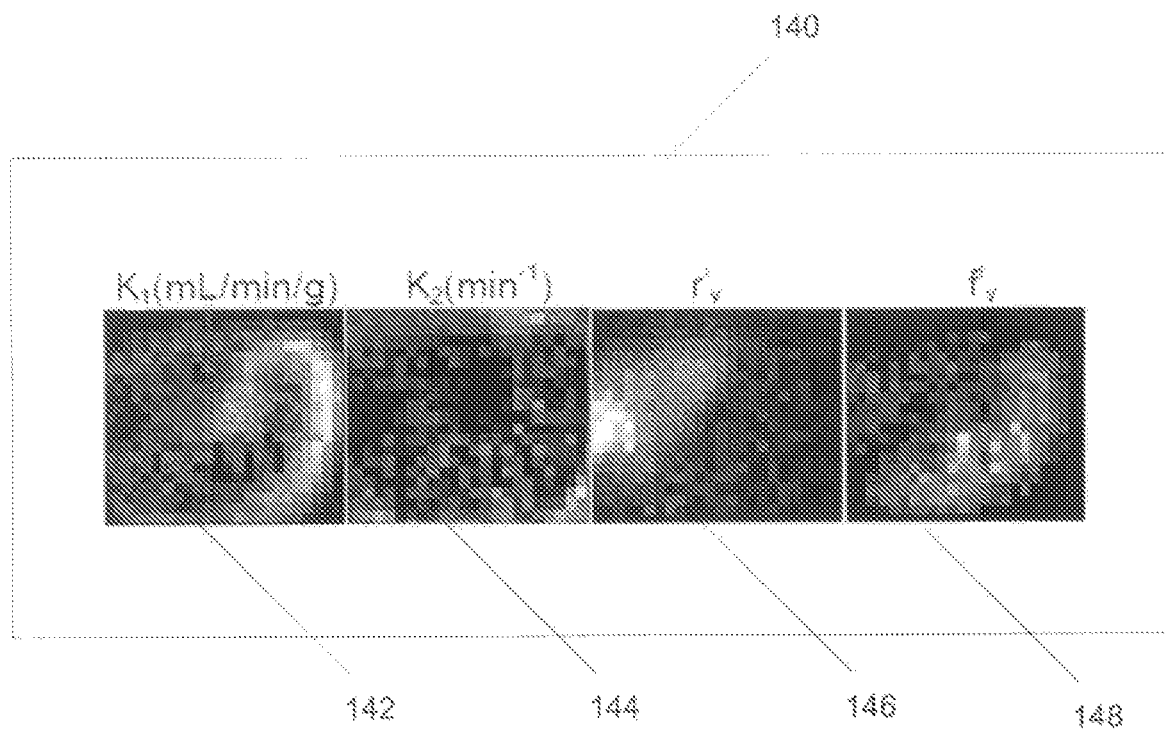
FIG. 9 shows parametric images of myocardial tissue extraction and egress as well as RV and LV contributions derived from the generalized-factor-analysis-estimated activity curves shown in FIG. 8.

FIG. 9 shows an image 142 of the absolute myocardial tissue extraction, $k_1$, an image 144 of the egress of flow out of the myocardium, $k_2$, an image 146 of the LV input function $f_v^i$, and an image 148 of the RV input function, $r_v^i$. The clear separation between the LV and RV factor images 146 and 148 indicates that they are unique solutions. By analyzing the image of the egress flow, $k_2$, a skilled operator may readily determine whether or not a disease or abnormal condition of the heart exists. The images 142, 144, 146, and 148 were obtained with a short acquisition time (5 seconds per the dynamic frame) and without post-reconstruction filtering. The images 142, 144, 146, and 148 indicate that generalized factor analysis and compartmental analysis are robust to noise. The images 142, 144, 146, and 148 also indicate that generalized factor analysis and compartmental analysis could yield useful results in the form of functional polar maps with even less noise, as voxels would be averaged in such a display. As expected, in those patients in which the LV and RV input functions were estimated with generalized factor analysis, the $k_2$ values were low (between approximately 0.012 and 0.028 min$^{-1}$). The corresponding $k_1$ values ranged between approximately 0.52 ml/min/g in patients with suspected coronary artery disease (CAD) and approximately 1.03 ml/min/g in patients with no suspected CAD at rest. The corresponding range of $k_1$ values at stress was between approximately 0.78 and 1.84 ml/min/g. Furthermore, $k_1$ values estimated in anterior, inferior, lateral and septal walls did not differ significantly (NS, paired t-test) in patients with normal myocardial blood perfusion (SSS=0). The flow values ($k_1$) estimated using the LV and RV input functions estimated by VOI analysis were consistently greater (8.3% to 27.6%) than those obtained using generalized factor analysis LV and RV input functions (p<0.05) where "p" is the "statistical significance" of the estimate. The statistical significance is the probability of an observed relationship (e.g., between variables) or a difference (e.g., between means) in a sample occurring by pure chance. In other words, the statistical significance of a result signifies the degree to which the result is "true" in the sense of being "representative of the population." The $k_2$ values associated with VOI were slightly greater (5-10%) than those with generalized factor analysis. However $f_v$ (0.39±0.07) and $r_v$ (0.31±0.02) parameters were significantly greater (13.4 to 31.7%) with VOI analysis than they were with generalized factor analysis (p<0.05). The coronary flow reserve (CFR) was also calculated as the ratio of flow at peak stress and flow at rest ($k_1$ stress/$k_1$ rest). CFR values ranged from 1.58 to 2.3 in patients with no prior known CAD and from 1.39 to 1.51 in patients with known prior CAD. $k_1$ and $k_2$ values were not strongly correlated at rest or stress ($r^2<0.69$), where $r^2$ is the squared multiple correlation.

Figure 10:
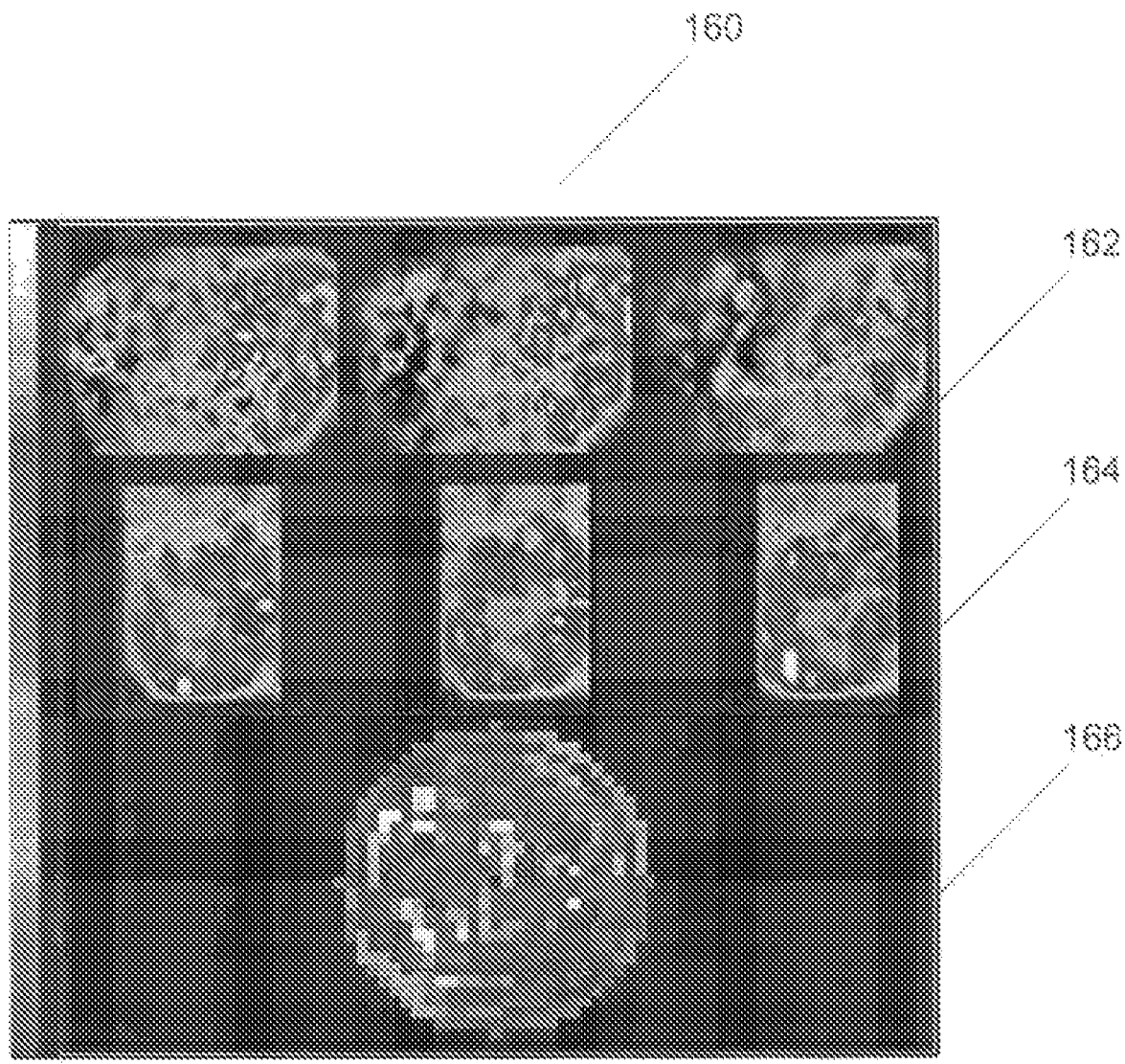
FIG. 10 shows a $k_1$ parametric map representing myocardial blood flow derived from the generalized-factor-analysis-estimated activity curves shown in FIG. 8.

FIG. 10 shows a parametric $k_1$ map 160 obtained from the patient studies. The parametric $k_1$ map 160 includes a transverse map 162, a short axis map 164, and a polar map 166.

Figure 11:
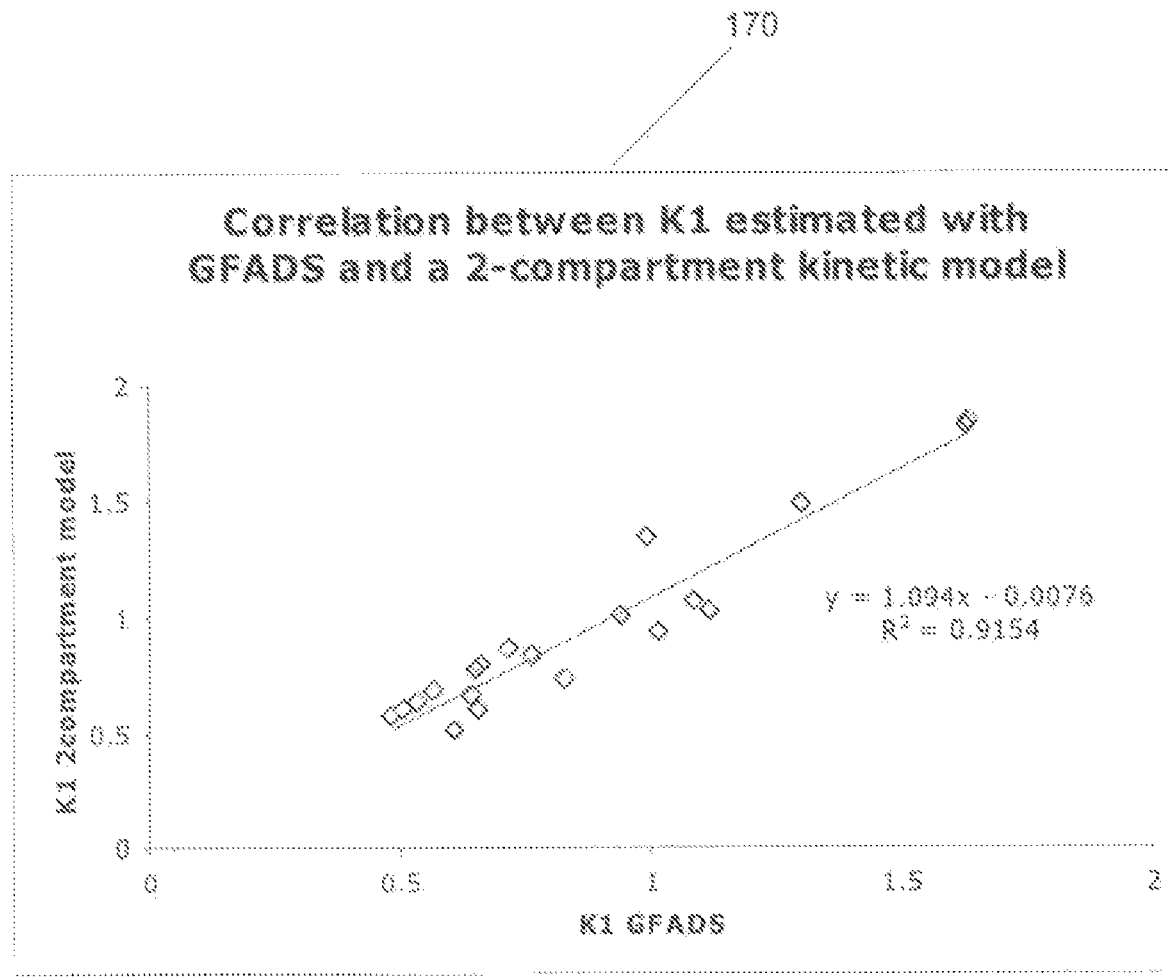
FIG. 11 shows a correlation between $k_1$ values estimated with generalized factor analysis and $k_1$ values estimated using a two-compartment kinetic model.

In the rest/stress patient studies, the compartmental analysis approach yielded robust estimates of myocardial blood flow that correlated very well with the parametric values measured using an independent two-compartment approach in which the myocardial blood flow was estimated on a voxel basis using LV and RV input functions only (bias=6.71±12.27%, y=1.09X−0.01, $r^2$=0.92). FIG. 11 shows a plot 170 depicting the correlation between $k_1$ values estimated by non-linear fitting of myocardial activity curves estimated with generalized factor analysis and $k_1$ values estimated by a two-compartment model using LV and RV input functions only.

Discussion

A generalized factor analysis approach was used to non-invasively estimate the LV and RV input functions from the dynamic $^{82}$Rb PET studies. After fitting the time-varying factor model to the dynamic data using a least-squares objective function, a different objective function, one which penalized spatial overlap between factor images, was minimized. The optimization preserved the least-squares fit obtained in the first estimation procedure and incorporated non-negativity constraints on the factors, as well as on the factor images. The generalized factor analysis approach does not require a priori knowledge of the kinetics and can be used in other dynamic imaging applications.

Furthermore, the generalized factor analysis approach does not require drawing volumes of interest to obtain the LV and RV activity-curve input functions. Only a cube that represents a cropped volume containing the heart is needed. This is advantageous, except for an initial definition of a volume comprising the heart, because it obviates the need for manual intervention in the quantitation scheme and makes the LV and RV activity-curve input functions reproducible. Furthermore, the estimates obtained with generalized factor analysis were significantly more accurate than activity curves obtained using a VOI approach, suggesting that the spillover and tissue overlap are the sources of significant errors with the latter approach.

The spillover from the LV compartment to the myocardium was greatest for activity curves obtained using a VOI approach at the lowest values of simulated blood flow, suggesting that the largest estimation errors are made when blood flow is reduced by disease. Furthermore, generalized factor analysis provides independent factor images of the LV, RV and myocardium. Therefore, the process of fitting the kinetic model to Equation 8 using the activity curves derived from generalized factor analysis subtracts the influence of LV and RV blood from the myocardial contribution. This makes a partial volume correction for spillover unnecessary. Therefore, a spillover due to myocardial contamination by the input function or due to cardiac motion translates into an overestimation of $f_v^i$ and $r_v^i$ but not of $k_1$ or $k_2$.

Finally, the generalized factor analysis estimates were more robust to noise than those obtained using VOI quantitation. This is consistent with the fact that the VOI quantitation is based on fewer voxels than the factor model, for which each time point of the curve estimated with generalized factor analysis results from fitting the entire image of corresponding factor coefficients to the data at that time point.

Although the number of factors must be defined before performing generalized factor analysis, using three factors (P=3) yields robust estimates of the LV and RV input functions in the Monte Carlo simulations and patient studies. This is consistent with the fact that the first three eigenvectors, obtained by principal component analysis, were consistently several times greater than the other eigenvectors in both Monte Carlo simulations and patient studies. This is also consistent with previous results performed with three factors (P=3) in teboroxime cardiac canine studies and ischemic patients.

In the Monte Carlo simulations, cross-planes were not included. This resulted in lower sensitivity but better axial spatial resolution than in the clinical studies. Positron range was modeled using an analytical approach. Modeling positron range is useful in PET Monte Carlo simulations of $^{82}$Rb, because the FWHM of the positron range is 2.6 mm as compared to 1 mm for $^{18}$F. As a result, the effect of positron range on spatial resolution and image quality is greater for $^{82}$Rb than for $^{18}$F. Likewise, modeling random coincidences is useful in the case of $^{82}$Rb-cardiac PET both because of the high counting rates following injection of 60 mCi of $^{82}$Rb, and because of the torso attenuation.

Dead-time is another factor that affects singles and coincidences differently. In the Monte Carlo simulations, patient-derived activity curves were used to generate spatially uniform LV and RV compartments. In these cases, generalized factor analysis yielded accurate estimates of the original simulated activity curves with very little overlap between LV, RV and myocardium.

When the dynamic activity does not vary uniformly within these structures one factor might be insufficient to describe the dynamic activity distribution in both the left and/or right ventricles. In these cases, more factors may be needed to fully describe the dynamic ventricular activities. The compartmental analysis approach described in FIG. 4 may model such situations. The grouping algorithm described in FIG. 5 does not necessarily result in spatially contiguous clusters, as the distance metric is not a spatial distance vector. This allows different locations within a given structure to have different kinetic parameters, a desirable property when non-uniform dynamic activity distributions, such as those in diseased patients, are to be modeled.

However, in the presence of respiratory motion, the lack of spatial constraints in the orthogonal grouping can lead to similar time curves that represent different tracer kinetics. One potential solution to this problem is to use spatial constraints in the orthogonal analysis. The differences in tissue count recovery, whether due to partial volume effect or to cardiac motion, affect only the estimation of $f_v$ and $r_v$. They do not affect the estimation of $k_1$ and $k_2$ by orthogonal grouping, as shown earlier.

In patient studies, a generalized factor analysis approach yielded LV and RV input functions of the expected form, and the two-compartment kinetic model yielded parametric maps of myocardial tissue extraction and egress, as well as spillover fractions from the blood pool into the myocardial tissue. Coronary flow reserve (CFR) was systematically higher in subjects with no prior known CAD (2.1±0.3) than in patients with known prior CAD (1.4±0.1). The estimated CFR values in subjects without obstructive CAD (FIG. 7) were somewhat lower than those usually found in the literature (~2.5). This may have been because these subjects already had multiple coronary risk factors (e.g., hypertension, dyslipidemia, diabetes). Furthermore, as flow increased, myocardial extraction would no longer have been proportional to flow, and peak flow would have been underestimated in dipyridamole studies. The flow dependency of the first pass extraction fraction can be modeled in the kinetic modeling approach described in FIG. 3 after estimating the LV and RV input functions with generalized factor analysis. The flow dependency can also be modeled using a post-processing step.

In subjects with known CAD who underwent dipyridamole stress, $k_1$ was 30% to 50% lower when the volume of interest drawn on the parametric image corresponded to a region irrigated by a stenotic vessel than it was when the volume of interest was drawn over a large myocardial area. Therefore, the generalized factor analysis and compartment analysis allowed discrimination between normal and diseased myocardial blood flow in different subjects, as well as in the same subject. Although generalized factor analysis taken alone may not allow the discrimination between different myocardial regions in the same patient (because only one factor is currently being used to model the myocardial time activity curve), the combination of the generalized factor analysis and compartment analysis approaches allows this aim to be achieved by using generalized factor analysis to estimate the LV and RV input functions, and then by estimating $k_1$ values on a voxel-by-voxel basis.

Quantitative dynamic $^{82}$Rb PET without arterial sampling is feasible using generalized factor analysis of dynamic sequences and compartmental modeling of $^{82}$Rb kinetics. In some studies, the generalized factor analysis technique accurately estimated parameters of absolute myocardial perfusion and kinetics with errors of less than 10%.

A number of embodiments of the invention have been described. Nevertheless, it will be understood that various modifications may be made without departing from the scope of the claims. For example, the methods and systems described above are not restricted to cardiac imaging and can be used to obtain unique activity curves and factor images solutions from other physiological regions such as the brain and the liver. Accordingly, other embodiments are within the scope of the following claims.

What is claimed is:

1. A method for estimating kinetic parameters from image data, the method comprising: using a processor for executing instructions for,
providing a model of kinetic contributions from first and second physiological regions;
grouping voxels of the image data into first and second groups;
determining an average value of the factors associated with the first group, the factors corresponding to blood-flow time activity curves;
incorporating the average value into the model;
estimating the kinetic parameters based on the model;
determining a first seed voxel for which a sum of distances between the first seed voxel and other voxels of the image data is greatest; and
selecting, from ungrouped voxels, a first predefined number of ungrouped voxels that are located nearest to the first seed voxel; and
wherein grouping voxels of the image data into the first group comprises defining a first group that includes the selected ungrouped voxels and the first seed voxel.

2. The method of claim 1, further comprising providing input functions to the model, the input functions comprising factors determined for the first and second physiological regions.

3. The method of claim 1, further comprising reducing a vector space spanned by the voxels to a subspace within the vector space, the subspace being defined by principal vectors of the voxels.

4. The method of claim 1, further comprising:
determining a second seed voxel for which a sum of distances between the second seed voxel and other voxels of the image data is greatest, the other voxels being remaining ungrouped voxels;
selecting, from the remaining ungrouped voxels, a second predefined number of ungrouped voxels that are located nearest to the second seed voxel; and
wherein grouping voxels of the image data into the second group comprises defining a second group that includes the selected remaining ungrouped voxels and the second seed voxel.

5. The method of claim 4, further comprising selecting the first predefined number to be equal to the second predefined number.

6. The method of claim 1, further comprising:
determining ungrouped voxels located within a minimum distance from the first seed voxel; and
wherein grouping voxels of the image data into the first group comprises grouping the ungrouped voxels and the first seed voxel.

7. The method of claim 1, wherein
providing the model comprises selecting the model to be a two-compartment model of myocardial factors and of kinetic contributions from a ventricle and a right ventricle; and
wherein estimating the kinetic parameters comprises determining extraction and egress rates of transport between myocardial tissue and freely diffusible space.

8. A method for estimating kinetic parameters from image data, the method comprising: using a processor for executing instruction for,
providing a model of kinetic contributions from first and second physiological regions;
determining a first seed voxel for which a sum of distances between the first seed voxel and other voxels of the image data is greatest;
selecting, from ungrouped voxels, a first predefined number of ungrouped voxels that are located nearest to the first seed voxel;
grouping voxels of the image data into first and second groups, wherein the first group includes the selected ungrouped voxels and the first seed voxel;
determining an average value of the factors associated with the first group;
incorporating the average value into the model; and
estimating the kinetic parameters based on the model.

9. The method of claim 8, further comprising:
determining a second seed voxel for which a sum of distances between the second seed voxel and other voxels of the image data is greatest, the other voxels being remaining ungrouped voxels;

selecting, from the remaining ungrouped voxels, a second predefined number of ungrouped voxels that are located nearest to the second seed voxel; and wherein grouping voxels of the image data into the second group comprises defining a second group that includes the selected remaining ungrouped voxels and the second seed voxel.

10. The method of claim 9, further comprising selecting the first predefined number to be equal to the second predefined number.

11. A method for estimating kinetic parameters from image data, the method comprising: using a processor for executing instructions for, provided a model of kinetic contributions from first and second physiological regions;

determining a first seed voxel for which a sum of distances between the first seed voxel and other voxels of the image data is greatest;

determining ungrouped voxels located within a minimum distance from the first seed voxel;

grouping voxels of the image data into the first group and second groups, wherein the first group includes the selected ungrouped voxels and the first seed voxel;

determining an average value of the factors associated with the first group;

incorporating the average value into the model; and estimating the kinetic parameters based on the model.

12. The method for estimating kinetic parameters from image data, the method comprising: using a processor for executing instructions for, providing a model of kinetic contributions from first and second physiological regions, wherein providing the model includes selecting the model to be a two-compartment model of myocardial factors and of kinetic contributions from a left ventricle and a right ventricle;

grouping voxels of the image data into first and second groups;

determining an average value of the factors associated with the first group;

incorporating the average value into the model; and estimating the kinetic parameters based on the model, wherein estimating the kinetic parameters includes determining extraction and egress rates of transport between myocardial tissue and freely diffusible space.

* * * * *

UNITED STATES PATENT AND TRADEMARK OFFICE
CERTIFICATE OF CORRECTION

| | | |
|---|---|---|
| PATENT NO. | : 7,519,211 B2 | Page 1 of 1 |
| APPLICATION NO. | : 11/533145 | |
| DATED | : April 14, 2009 | |
| INVENTOR(S) | : Georges El Fakhri | |

It is certified that error appears in the above-identified patent and that said Letters Patent is hereby corrected as shown below:

At col. 15, line 62, delete the word "the" as follows:

grouping voxels of [[the]] image data into first and second

At col. 16, line 39, insert --:-- as follows:

7. The method of claim 1, wherein:

At col. 16, line 42, insert the word --left-- as follows:

kinetic contributions from a left ventricle and a right ven-

At col. 17, line 23, delete the words "the" and "group" as follows:

grouping voxels of [[the]] image data into the first [[group]] and

At col. 18, line 6, replace the word "The" with "A" as follows:

12. [[The]] A method for estimating kinetic parameters from

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,519,211 B2 | Page 1 of 1 |
| APPLICATION NO. | : 11/533145 | |
| DATED | : April 14, 2009 | |
| INVENTOR(S) | : Georges El Fakhri and Arkadiusz Sitek | |

It is certified that error appears in the above-identified patent and that said Letters Patent is hereby corrected as shown below:

In the Specification

Column 1, Line 12, insert -- STATEMENT OF FEDERALLY SPONSORED RESEARCH
This invention was made with government support under Grant No. EB005876 awarded by the National Institutes of Health. The government has certain rights in the invention. --

Signed and Sealed this
Twenty-third Day of May, 2023

Katherine Kelly Vidal
*Director of the United States Patent and Trademark Office*